United States Patent [19]

Kai et al.

[11] Patent Number: 5,510,513
[45] Date of Patent: Apr. 23, 1996

[54] FLUORINE CONTAINING DIESTER OF ALKYL-OR ALKENYLSUCCINIC ACID, PREPARATION THEREOF AND MAGNETIC RECORDING MEDIUM

[75] Inventors: Yoshiaki Kai, Neyagawa; Kiyosi Takahasi, Ibaraki; Yukikazu Ohchi, Kadoma, all of Japan

[73] Assignee: Matsushita Electric Industrial Co., Ltd., Osaka, Japan

[21] Appl. No.: 223,001

[22] Filed: Apr. 5, 1994

[30] Foreign Application Priority Data

Apr. 5, 1993 [JP] Japan ................. 5-077819

[51] Int. Cl.$^6$ ................. C07C 69/40; C07C 69/52
[52] U.S. Cl. ................. 560/197
[58] Field of Search ................. 560/197

[56] References Cited

FOREIGN PATENT DOCUMENTS

| 0473871 | 3/1992 | European Pat. Off. . |
| 0563791 | 10/1993 | European Pat. Off. . |
| 63-183607 | 7/1988 | Japan . |
| 2-148413 | 6/1990 | Japan . |

Primary Examiner—José G. Dees
Assistant Examiner—Joseph M. Conrad, III
Attorney, Agent, or Firm—Wenderoth, Lind & Ponack

[57] ABSTRACT

A fluorine containing diester of an alkyl- or alkenylsuccinic acid having the general formula:

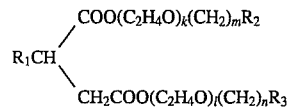

wherein $R_1$ represents an alkyl or alkenyl group, at least one of $R_2$ and $R_3$ is a fluoroalkyl or fluoroalkenyl group, the remaining of $R_2$ and $R_3$ is an alkyl or alkenyl group, k, l, m and n are 0 or an integer not less than 1, respectively, and k+l are an integer of not less than 2, which provides an excellent lubricating property under any environment from low humidity to high humidity, and is particularly suitable for use in a magnetic recording medium.

2 Claims, No Drawings

FLUORINE CONTAINING DIESTER OF ALKYL-OR ALKENYLSUCCINIC ACID, PREPARATION THEREOF AND MAGNETIC RECORDING MEDIUM

FIELD OF THE INVENTION

The present invention relates to a novel fluorine containing compound which is useful as a surfactant, a lubricant, a releasing agent, a rust preventive, etc. for precision machineries and components requiring high lubricity, a process for preparing the same, and a magnetic recording medium comprising the same.

DESCRIPTION OF THE PRIOR ART

As machines and their components have become small in size and the high-precision thereof are required, the lubricating manner in sliding portions thereof is being changed from fluid lubrication to boundary lubrication. Particularly, in electronic equipments and components, such as VTR, magnetic disks and the like, the adoption of ferromagnetic metal thin films to improve recording density requires a high degree of lubricity for the sliding between a magnetic tape or disk and a magnetic head.

For example, in depositon recording tapes film and hard disks, the lubricant layer on a magnetic layer surface is formed in such a way that it has a thickness as low as scores of angstrom in order to minimize spacing loss between the magnetic recording medium and the magnetic head to provide high power output while ensuring durability and reliability. Therefore, it is a crucial problem to develop organic compounds excellent in lubricity as a material which forms the lubricating agent layer.

As the lubricant for a metal thin film-type magnetic recording medium, a fluoroalkyl group containing ester of an aliphatic carboxylic acid, for example, a compound having the formula:

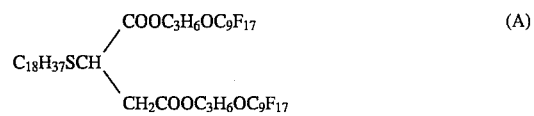

a compound having the general formula:

wherein $R_4$ represents an alkyl group, and $R_5$ and $R_6$ independently represent a fluoroalkyl group or alkyl group, and a nonionic surfactant containing perfluoroalkenyl group having the general formula $$C_pF_{2p-1}O(C_qH_{2q}O)_rR_7 \quad (C)$$

wherein $R_7$ represents hydrogen, a substituted or unsubstituted hydrocarbon group, or a substituted or unsubstituted acyl group, p is an integer from 3 to 18, q is 2 or 3 and r is an integer from 3 to 25, are proposed since they have an excellent compatibility with metal thin film (see Japanese Patent Kokai Nos. 148413/1990, 291185/1991 and 183607/1988).

However, the lubricant comprising the fluoroalkyl group containing ester of an aliphatic carboxylic acid having the formula (A) or (B) or the nonionic surfactant containing perfluoroalkenyl group having the formula (C) has the problem that lubricity is decreased under high humidity environment.

SUMMARY OF THE INVENTION

It is an object of the present invention to provide a substance which gives excellent lubricity under any environment from low humidity to high humidity.

It is another object of the present invention to provide a process for preparing such substance.

It is a further object of the present invention to provide a magnetic recording medium having excellent lubricity under any environment from low humidity to high humidity.

The present invention provides a fluorine containing diester of an alkyl- or alkenylsuccinic acid having the general formula:

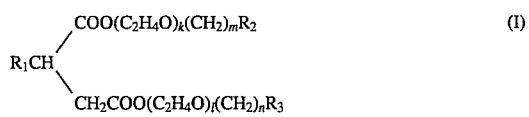

wherein $R_1$ represents an alkyl or alkenyl group, at least one of $R_2$ and $R_3$ are a fluoroalkyl or fluoroalkenyl group, the rest of $R_2$ and $R_3$ is an alkyl or alkenyl group, k, l, m and n are 0 or an integer of not less than 1, respectively, and k+l are an integer of not less than 2.

The present invention also provides a process for preparing the fluorine containing diester of an alkyl- or alkenylsuccinic acid having the general formula (I) from an alkyl- or alkenylsuccinic acid or anhydride and a fluorine containing alcohol.

The present invention also provides a magnetic recording medium in which a ferromagnetic layer is formed on a non-magnetic support, and a lubricant layer comprising at least one fluorine containing diester of an alkyl- or alkenylsuccinic acid having the general formula (I) is formed directly or through a protective film on the ferromagnetic film.

DETAILED DESCRIPTION OF THE INVENTION

In the fluorine containing ester of an alkyl- or alkenylsuccinic acid having the formula (I), $R_1$ is an alkyl or alkenyl group containing 6 to 30 carbon atoms, preferably 10 to 24 carbon atoms. When the number of the carbon atoms is less than 6 or more than 30, lubricity is lowered. $R_2$ and $R_3$ contain 2 to 30 carbon atoms, preferably 4 to 20 carbon atoms, respectively. When the number of the carbon atoms is 1 or more than 30, the lubricity is also lowered. k+l is from 2 to 20, preferably from 3 to 10. When k+l is 1 or more than 20, the lubricity is also lowered. m and n are from 0 to 20, preferably from 0 to 12, respectively. When m or n exceeds 20, the lubricity is also lowered.

The fluorine containing ester of an alkyl- or alkenylsuccinic acid according to the present invention may be prepared in several manners.

In a first method, an alkyl- or alkenylsuccinic acid anhydride of the general formula:

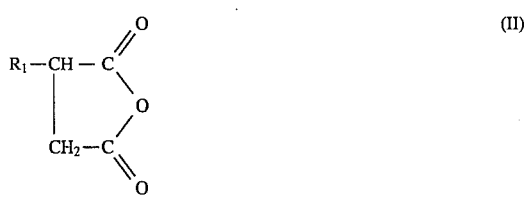

wherein $R_1$ represents an alkyl or alkenyl group,
is reacted with an adduct of a fluoroalkyl or fluoroalkenyl alcohol and ethylene oxide of the general formula:

$$R(CH_2)_x(OC_2H_4)_yOH \qquad (III)$$

wherein R represents a fluoroalkyl or fluoroalkenyl group, x is 0 or an integer of not less than 1, and y is an integer of not less than 1, to form a monoester of an alkyl- or alkenylsuccinic acid.

A molar ratio of the alkyl- or alkenylsuccinic anhydride to the adduct of a fluoroalkyl or fluoroalkenyl alcohol and ethylene oxide is usually from 0.5 to 2.

The reaction is carried out at a temperature of from 40° to 150° C., preferably from 60° to 120° C., preferably in the presence of a solvent. Suitable solvents are hydrophobic solvents which can dissolve the reactants, such as benzene, excluding alcohols and esters. In addition, the solvent to be used should ensure the above reaction temperature. That is, the solvents having too low boiling point are not preferred. This applies to the solvents used in all the reactions below.

The monoester is then reacted with an alcohol selected from the group consisting of an alkyl or alkenyl alcohol, an adduct of an alkyl or alkenyl alcohol and ethylene oxide, a fluoroalkyl or fluoroalkenyl alcohol, or an adduct of a fluoroalkyl or fluoroalkenyl alcohol and ethylene oxide having the general formula (III), which is different in composition from the above adduct of a fluoroalkyl or fluoroalkenyl alcohol and ethylene oxide, in the presence of an acidic catalyst to form the fluorine containing diester of an alkyl- or alkenylsuccinic acid according to the present invention of the general formula (I), in which $R_2$ is different from $R_3$.

Examples of acidic catalysts are mineral acids such as sulfuric acid, hydrochloric acid, etc., organic acids such as aromatic sulfonic acids, and Lewis acids such as boron fluoride etherate. The acidic catalyst ia used in an amount of 1 to 5% by weight, based on the total weight of the monoester and the alcohol.

A molar ratio of the monoester to the alcohol is usually from 0.5 to 2.

The reaction is usually carried out at a temperature of from 40° to 150° C., preferably from 60° to 120° C., preferably in the presence of a solvent. Suitable solvents are hydrophobic solvents which can dissolve the reactants, such as benzene, excluding alcohols and esters.

In a second method, the alkyl- or alkenylsuccinic anhydride of the general formula (II) is reacted at first with an alcohol selected from the above group to form a monoester of an alkyl- or alkenylsuccinic acid.

Then, the monoester is reacted with an adduct of a fluoroalkyl or fluoroalkenyl alcohol and ethylene oxide having the general formula (III) in the presence of an acidic catalyst to form the fluorine containing diester of an alkyl- or alkenylsuccinic according to the present invention of the general formula (I).

The reaction may be carried out under the similar condition to that in the first method.

In a third method, an alkyl- or alkenylsuccinic anhydride of the general formula (II) is reacted with an adduct of a fluoroalkyl or fluoroalkenyl alcohol and ethylene oxide having the general formula (III) in the presence of an acidic catalyst to obtain in one step the fluorine containing diester of an alkyl- or alkenylsuccinic acid according to the present invention of the general formula (I), in which $R_2$ is equal to $R_3$ and both of them are fluoroalkyl groups.

The acidic catalysts used are the same as above. A molar ratio of the alkyl- or alkenylsuccinic anhydride to the adduct of a fluoroalkyl- or alkenyl alcohol and ethylene oxide is usually from 0.5 to 2.

The reaction is carried out at a temperature of from 40° to 150° C., preferably from 60° to 120° C., preferably in the presence of a solvent. Suitable solvents are hydrophobic solvents which can dissolve the reactants such as benzene, excluding alcohols esters.

In a fourth method, an alkyl- or alkenylsuccinic acid is used in place of the alkyl- or alkenylsuccinic anhydride. That is, the alkyl- or alkenylsuccinic acid is reacted with an adduct of a fluoroalkyl or fluoroalkenyl alcohol and ethylene oxide having the general formula (III) in the presence of an acidic catalyst to obtain in one step the fluorine containing diester of an alkyl- or alkenylsuccinic acid according to the present invention of the general formula (I).

The reaction may be carried out under the similar conditions described above.

In a fifth method, an alkyl- or alkenylsuccinic anhydride of the general formula (II) is reacted with an adduct of a fluoroalkyl or fluoroalkenyl alcohol and ethylene oxide of the general formula (III) to form a monoester of an alkyl- or alkenylsuccinic acid.

Then, the monoester of an alkyl- or alkenylsuccinic acid obtained is chlorinated with a chlorinating agent to form a monoester of an alkyl- or alkenylsuccinic acid chloride.

Examples of chlorinating agents are inorganic halogen compounds such as phosphoryl chloride, thionyl chloride, phosphorous pentachloride, phosphorus chloride and the like. The chlorinating agent is usually used in an amount of from 3 to 30 equivalents per mole of the monoester.

The reaction is carried out at a temperature of from 40° to 150° C., preferably from 60° to 120° C., preferably in the presence of a solvent. Suitable solvents are hydrophobic solvents which can dissolve the reactants, such as benzene, excluding alcohols and esters.

Thereafter, the monoester of the alkyl- or alkenylsuccinic acid chloride obtained is reacted with an alcohol selected from the group consisting of an alkyl or alkenyl alcohol, an adduct of an alkyl or alkenyl alcohol and ethylene oxide, a fluoroalkyl or fluoroalkenyl alcohol, or an adduct of a fluoroalkyl or fluoroalkenyl alcohol and ethylene oxide having the general formula (III), which is different in composition from the above adduct of a fluoroalkyl- or alkenyl alcohol and ethylene oxide, in the presence of an alkaline catalyst to form the fluorine containing diester of an alkyl- or alkenylsuccinic acid according to the present invention of the general formula (I).

A molar ratio of the monoester of the alkyl- or alkenylsuccinic acid chloride to the alcohol is usually from 0.5 to 2.

Examples of alkaline catalyst are pyridine, triethylamine, zinc chloride, iodine, etc. They are used in an amount of from 1 to 10 equivalents per mole of the acid chloride.

The reaction is carried out at a temperature of from 40° to 150° C., preferably from 60° to 120° C., preferably in the presence of a solvent. Suitable solvents are hydrophobic solvents which can dissolve the reactants such as benzene, excluding alcohols and esters.

In a sixth method, an alkyl- or alkenylsuccinic anhydride of the general formula (II) is reacted with an alcohol selected from the group consisting of an alkyl or alkenyl alcohol, an adduct of an alkyl or alkenyl alcohol and ethylene oxide, a fluoroalkyl or fluoroalkenyl alcohol, or an adduct of a fluoroalkyl or fluoroalkenyl alcohol and ethylene oxide having the general formula (III) to form a monoester of an alkyl- or alkenylsuccinic acid.

Then, the monoester of an alkyl- or alkenylsuccinic acid obtained is chlorinated with a chlorinating agent to form a monoester of an alkyl- or alkenylsuccinic acid chloride.

Thereafter, the monoester of an alkyl or alkenylsuccinic acid chloride is reacted with an adduct of a fluoroalkyl or fluoroalkenyl alcohol and ethylene oxide having the general formula (III), which is different in composition from the above adduct of a fluoroalkyl or fluoroalkenyl alcohol and ethylene oxide having the general formula (III), in the presence of an alkaline catalyst to form the fluorine containing diester of an alkyl- or alkenylsuccinic acid according to the present invention of the general formula (I). The reaction may be carried out under the similar condition to that in the fifth method.

The present invention also relates to a magnetic recording medium in which a ferromagnetic layer is formed on a non-magnetic support, and a lubricant layer comprising at least one fluorine containing diester of an alkyl- or alkenylsuccinic acid having the general formula (I) is formed directly or through a protective film on the ferromagnetic film.

The lubricant layer is a thin layer comprising at least one fluorine containing diester of an alkyl- or alkenylsuccinic acid having the general structure (I) alone or in admixture with other lubricating agent, a rust preventive and the like. The fluorine containing diester of an alkyl- or alkenylsuccinic acid according to the present invention is used in an amount of from 0.05 to 100 mg, preferably from 0.1 to 50 mg per square centimeter of the layer surface. The other lubricating agent and rust preventive mentioned above are preferably fluorine containing compounds, more preferably those in the form of fluid. They may be used in a ratio of from 0 to 80%, preferably from 0 to 70%, based on of the mixture of the fluorine containing diester of an alkyl- or alkenylsuccininc acid and the other lubricant and/or rust preventive. When the fluorine containing diester of an alkyl- or alkenylsuccinic acid according to the present invention is less than 20%, it is difficult to achieve the advantageous results of the present invention.

As the protective film, an amorphous, graphite-like, or diamond-like carbon thin film which is formed by sputtering process, plasma CVD process and the like can be used alone or in admixture thereof, or in a laminated form thereof. The protective film has preferably a thickness of from 50 to 500 Å.

The fluorine containing diester of an alkyl- or alkenylsuccinic acid according to the present invention is different from conventional lubricants in that it has a fluoroalkyl or fluoroalkylene terminal group having ethylene oxide groups which are attached through alkylene groups to a fluorocarbon terminal group, i.e. the fluoroalkyl or alkenyl terminal group immediately after it, or that it has an alkyl or alkylene terminal group having ethylene oxide groups which are attached through alkylene groups to an aliphatic hydrocarbon group, i.e. the alkyl or alkenyl terminal group immediately after it.

It has been known hitherto that the ethylene oxide group is a polar group which is excellent in metal capturing ability. That is, the ethylene oxide group is strongly adsorbed on the surface of a metal portion of a metal thin film type magnetic recording medium, a thin film metal head or MIG (metal in gap) head. However, the ethylene oxide groups have a large number of hydrophilic ether linkages in the groups, hence absorbing water under high humidity environment. On the other hand, since the fluorocarbon group and the aliphatic hydrocarbon group are hydrophobic, the hydrophilicity of the ethylene oxide groups can be masked when they are bonded to the fluorocarbon group or the aliphatic group.

In order to ensure the masking effect, a molecule structure should be constructed in such a manner that an aliphatic hydrocarbon group unbound to the ethylene oxide groups exists in the same molecule, and a fluorocarbon group and an aliphatic hydrocarbon group bonded to the ethylene oxide groups exist at the molecule terminal, so that the ethylene oxide groups are wrapped in from the surroundings.

The fluorocarbon group is exposed on the surface of the metal thin film, the protective film, or the magnetic head to contribute to lower the energy of the surface and form a tack free surface, thereby developing a protecting action for the surface of the metal thin film or the magnetic head under a low humidity environment. The aliphatic hydrocarbon group gives good lubricating property since it has a flexible carbon-carbon linkage chain and is oriented by an appropriate intermolecular interaction with hydrocarbon chains in other neighboring molecules.

Therefore, the synergistic effect resulting from the balanced existence of such the terminal group and the polar groups provides an excellent lubricating property under any environment from low humidity to high humidity.

EXAMPLES

The present invention will be illustrated by Examples and Comparative Examples more specifically.

Example 1

Into a 1 liter flask equipped with an agitating element, 35.3 g (0.10 mole) of octadecylsuccinic anhydride, 68.4 g (0.10 mole) of an adduct of a fluoroalkyl alcohol and ethylene oxide having the formula $C_8F_{17}(CH_2)_2(OC_2H_4)_5OH$, and 300 ml of benzene were charged and reacted under reflux for 24 hours. After the reaction was completed, the benzene was distilled off from the reaction mixture. Furthermore the residue was dissolved in n-hexane and cooled to 0° C. to remove the unreacted octadecylsuccinic anhydride. The residue is dissolved in methanol, followed by the similar treatment to remove the unreacted adduct of a fluoroalkyl alcohol and ethylene oxide to obtain 71 g of a monoester of octadecylsuccinic acid.

Into a 1 liter flask equipped with a water separator and an agitating element, 51.9 g (0.05 mole) of the monoester, 7.8 g (0.05 mole) of 9-decenol, 0.9 g (1.5% by weight, based on the weight of the reactants) of p-toluene sulfonic acid (referred to as PTS hereinafter) as an acidic catalyst and 300 ml of benzene were charged and reacted under reflux for 24 hours.

After the reaction was completed, the reaction mixture was repeatedly washed with distilled water until the value of pH became to 7, and then dried over anhydrous sodium sulfate. Then benzene was distilled off and 300 ml of methanal was added to the reaction mixture followed by washing it in a separatory funnel to remove the unreacted monoester and 9-decenol to obtain 42 g of a colorless transparent liquid. Infrared analysis (IR), gel permeation chromatography (GPC) and organic mass analysis (FD-MS) show that the colorless transparent liquid is a compound of the following formula which is free from the starting materials and by-products.

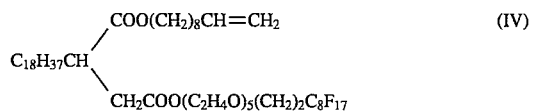

(MW: 1,175)

IR:

The absorption peaks at 1,775 $cm^{-1}$ corresponding to the acid anhydride and at 3,330 $cm^{-1}$ corresponding to the alcohol were disappeared and the absorption peak at 1,735 $cm^{-1}$ corresponding to the ester was appeared.

GPC:

None of the adduct of a fluoroallkyl alcohol and ethylene oxide, 9-decenol, octadecylsuccinic anhydride and the monoester thereof was detected.

FD-MS:

A main peak was observed at 1,175 of m/e.

Example 2

Into a 1 liter flask equipped with an agitating element, 35.3 g (0.10 mole) of octadecylsuccinic anhydride, 15.6 g (0.10 mole) of 9 decenol, and 300 ml of benzene were charged and reacted under reflux for 24 hours. After the reaction was completed, the benzene was distilled off from the reaction mixture. The residue was dissolved in n-hexane and cooled to −10° C. to remove the unreacted octadecylsuccinic anhydride. Further, the residue was dissolved in methanol, followed by the similar treatment: to remove the unreacted 9-decenol to obtain 47 g of monoester of octadecylsuccinic acid.

Into a 1 liter flask equipped with a water separator and an agitating element, 25.5 g (0.05 mole) of the monoester, 34.2 g (0.05 mole) of an adduct of a fluoroalkyl alcohol ant ethylene oxide having the formula $C_8F_{17}(CH_2)_2(OC_2H_4)_5OH$, 0.9 g (1.5% by weight, based on the weight of the reactants) of PTS and 300 ml of benzene were charged and reacted under reflux for 24 hours.

After the reaction was completed, the reaction mixture was treated and purified in the similar manner to that in Example 1 to obtain 41 g of a colorless and transparent liquid. The liquid is found to be the same compound as obtained in Example 1 having the formula (IV).

Example 3

In the similar manner as that in Example 1, 35.3 g (0.10 mole) of octadecylsuccinic anhydride was reacted with 68.4 g (0.10 mole) of an adduct of a fluoroalkyl alcohol and ethylene oxide having the formula $C_8F_{17}(CH_2)_2(OC_2H_4)_5OH$ to obtain 71 g of monoester of octadecylsuccinic acid.

51.9 g (0.05 mole) of the monoester and 60 g of thionyl chloride were charged into a 1 liter flask equipped with an agitating element and reacted under reflux for 3 hours. After the completion of the reaction, excessive thionyl chloride was removed from the reaction mixture under reduced pressure. 7.8 g (0.05 mole) of 9 decenol in a mixed solvent of 20 ml of pyridine and 300 ml of benzene was added dropwise thereto, followed by keeping the mixture at room temperature for 4 hours with stirring to complete the reaction.

After the completion of the reaction, the reaction mixture was washed with 300 ml of an aqueous 5% HCl solution to remove excessive pyridine from the reaction mixture. The mixture was then repeatedly washed with distilled water until a pH value of 7 was attained, followed by drying over anhydrous sodium sulfate. Then the purification procedure similar to that in Example 1 was carried out to obtain a colorless and transparent liquid. The liquid was found to be the identical compound with that in Example 1 having the formula (IV).

Example 4

13.3 g (0.05 mole) of 1-dodecenylsuccinic anhydride, 58.4 g of an adduct of a fluoroalkyl alcohol and ethylene oxide having the formula $C_6F_{13}(CH_2)_2(OC_2H_4)_5OH$, 2.2 g (3.0%, based on the weight of the reactants) of PTS and 300 ml of benzene were charged into a 1 liter flask equipped with a water separator and an agitating element, and reacted under reflux for 24 hours.

After the completion of the reaction, the reaction mixture was subjected to the purification procedure similar to that in Example 1 to obtain 57 g of a colorless transparent liquid. IR, GPC, and FD-MS analyses show that the liquid is the compound represented by the following formula which is free from the starting materials and byproducts.

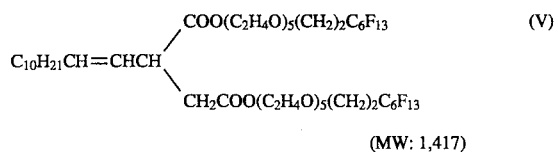

(MW: 1,417)

IR:

The absorption peaks at 1,775 cm$^{-1}$ corresponding to the acid anhydride and at 3,330 cm$^{-1}$ corresponding to the alcohol were disappeared, and the absorption peak at 1,735 cm$^{-1}$ corresponding to the ester was appeared.

GPC:

None of the adduct of a fluoroallkyl alcohol and ethylene oxide, 1-dodecenylsuccinic anhydride was detected.

FD-MS:

A main peak was observed at 1,417 of m/e.

Example 5

In this Example, 1-dodecenylsuccinic acid was used in place of 1-dodecenylsuccinic anhydride.

14.2 g (0.05 mole) of 1-dodecenylsuccinic acid, 58.4 g (0.10 mole) of the adduct of a fluoroalkyl alcohol and ethylene oxide having the formula $C_6F_{13}(CH_2)_2(OC_2H_4)_5OH$, 2.2 g (3.0%, based on the weight of the reactants) of PTS and 300 ml of benzene were charged into a 1 liter flask equipped with a water separator and an agitating element, and reacted under reflux for 24 hours.

After the completion of the reaction, the reaction mixture was subjected to the purification procedure similar to that in Example 1 to obtain 58 g of a colorless transparent liquid. The liquid was found to be the compound having the formula (V).

Example 6

A magnetic recording medium was prepared as follows: The non-magnetic support used in the magnetic recording medium was a polyester film which has particulate projections (having an average height of 70 Å, and a diameter of 1 μm) of a gentle slant composed of silica fine particles added in the film, in a number of several per 100 μm$^2$ of the film surface, in which comparatively large projections of microparticles derived from polymerization catalyst residues were decreased as much as possible. On the polyester film, steep mountain-like projections were formed in a number of 1×10$^7$ per square millimeter of the surface, using colloidal silica particles as nuclei and a UV cured epoxy resin as a binder, to obtain a non magnetic support.

A Co-Ni ferromagnetic film having a Ni content of 20% and a thickness of 1000 Å, was formed on the non magnetic support by successive vacuum diagonal deposition in the presence of a slight amount of oxygen. The oxygen content in the ferromagnetic film was 5% in atom fraction.

Then a lubricant layer was formed on the above ferromagnetic film by coating it with the fluorine containing diester of an alkylsuccinic acid having the formula (IV) in an amount of 10 mg per square meter to obtain a magnetic recording medium. The magnetic recording medium was cut to a predetermined width to prepare a magnetic tape.

The magnetic tape was applied to a commercial available video desk, and the output characteristics at repeated traveling were measured under the conditions of 23° C. and 10% RH and that of 40° C. and 80% RH, respectively, to determine traveling number of times at which RF output was decreased by 3 dB in comparison with an initial value thereof or an output fluctuation began to occur.

Example 7

Example 6 was repeated except that a compound of the formula (V) was used in place of the compound of the formula (IV).

Example 8

Example 6 was repeated except that a mixture of the compound of the formula (IV) and a known rust preventive having the formula $C_8F_{17}C_2H_4NHC_{18}H_{35}$ in a weight ratio of 2:1 was used in place of the compound of the formula (IV).

Example 9

Example 6 was repeated except that a mixture of a compound of the formula (V) and a known lubricating agent having the formula $C_{17}H_{33}COOC_2H_4C_6F_{13}$ in a weight ratio of 1:1 was used in place of the compound of the formula (IV).

Comparative Example 1

Example 6 was repeated except that a compound of the following formula (VI) was used in place of the compound of the formula (IV).

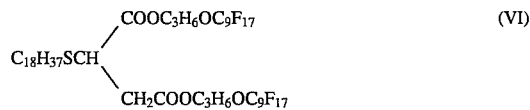

Comparative Example 2

Example 6 was repeated except that a compound of the following formula (VII) was used in place of the compound of the formula (IV).

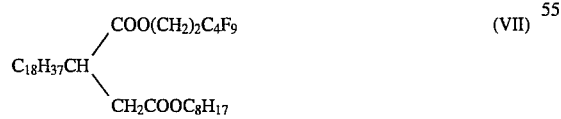

Comparative Example 3

Example 6 was repeated except that a compound of the following formula was used in place of the compound of the formula (IV).

TABLE 1

| Magnetic Tape | Traveling Number of Times | |
|---|---|---|
| | 23° C., 10% RH | 40° C., 80% RH |
| Example 1 | >200 | >200 |
| Example 2 | >200 | >200 |
| Example 3 | >200 | >200 |
| Example 4 | >200 | >200 |
| Comparative Example 1 | 100 | 130 |
| Comparative Example 2 | 60 | 70 |
| Comparative Example 3 | 40 | 20 |

Table 1 clearly shows that all the magnetic tapes comprising the lubricant layer comprising one or more fluorine containing diester of an alkyl- or alkenylsuccinic acid according to the present invention have an excellent repeated traveling number of times under low and high humidity conditions while the magnetic tapes comprising the lubricating agent layer comprising conventional lubricating agents have poor repeated traveling number of times under low and high humidity conditions.

Example 10

This Example illustrates another magnetic recording medium. A non-magnetic support was prepared by plating the surface of an Al alloy plate having a diameter of 95 mm and a thickness of 1.2 mm with non magnetic Ni-P alloy to a thickness of 25 μm, followed by texture processing to obtain a non-magnetic support having projections of 50 Å in average roughness and 300 Å in maximum height.

A ferromagnetic film comprising a Cr ground of 1300 Å in thickness and a Co-Ni layer of 600 Å in thickness was formed on the nonmagnetic Ni-P alloy plated support by sputtering process. A protective film of graphite having a thickness of 200 Å was formed on the ferromagnetic film by sputtering process (Sample A). Alternatively, a protective film of diamond-like carbon having a thickness of 50 Å was formed on the ferromagnetic film by plasma CVD process (Sample B).

Then a lubricant layer was formed on the protective film by coating it with a fluorine containing diester of an alkylsuccinic acid having the formula (IV) in an amount of 10 mg per square meter to obtain a magnetic recording disk.

CSS (contact start stop) tests were effected for the recording disk prepared above under the conditions of 23° C. and 10% RH and that of 40° C. and 80% RH, respectively, and the durability of the recording disk was evaluated by determining the CSS number of times at which the friction coefficient exceeded 1.0 or a head crash occurred.

Example 11

Example 10 was repeated except that a compound of the formula (V) was used in place of the compound of the formula (IV).

Example 12

Example 10 was repeated except that a mixture of the compound of the formula (IV) and a known rust preventive having the formula $C_8F_{17}C_2H_4NHC_{18}H_{35}$ in a weight ratio of 2:1 was used in place of the compound of the formula (IV).

Example 13

Example 10 was repeated except that a mixture of the compound of the formula (V) and a known lubricating agent having the formula $C_{17}H_{33}COOC_2H_4C_6F_{13}$ in a weight ratio of 1:1 was used in place of the compound of the formula (IV).

Comparative Example 4

Example 10 was repeated except that a compound of the formula (VI) was used in place of the compound of the formula (IV).

Comparative Example 5

Example 10 was repeated except that a compound of the formula (VII) was used in place of the compound of the formula (IV).

Comparative Example 6

Example 10 was repeated except that a compound of the following formula was used in place of the compound of the formula (IV).

$$C_9F_{17}O(C_2H_4O)_7CH_3$$

TABLE 2

| Magnetic Disk | Sample | CSS Number of Times 23° C., 10% RH | 40° C., 80% RH |
|---|---|---|---|
| Example 10 | A | >50,000 | >50,000 |
| Example 11 | B | >50,000 | >50,000 |
| Example 12 | A | >50,000 | >50,000 |
| Example 13 | B | >50,000 | >50,000 |
| Comp. Example 4 | A | 18,000 | 25,000 |
| Comp. Example 5 | B | 10,000* | 12,000 |
| Comp. Example 6 | A | 5,000* | 1,000 |

*Head crash occurred

Table 2 clearly shows that all the magnetic disks comprising the lubricating agent layer comprising one or more fluorine containing diester of an alkylsuccinic acid according to the present invention have an excellent CSS durability under low and high humidity conditions while the magnetic disks comprising the lubricating agent layer comprising conventional lubricating agents have poor CSS durability under low and high humidity conditions.

Similar results were obtained for the following compounds according to the present invention.

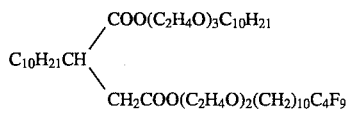
(VIII)

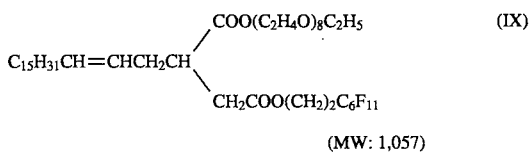
(IX)

(MW: 1,057)

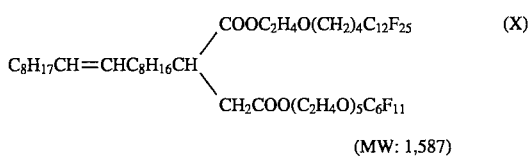
(X)

(MW: 1,587)

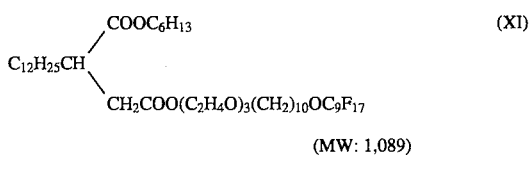
(XI)

(MW: 1,089)

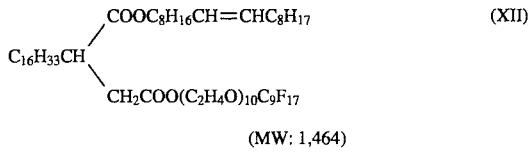
(XII)

(MW: 1,464)

As is clear from the foregoing description, the fluorine containing diester of an alkyl- or alkenylsuccininic acid provides an advantageous effect that lubricity is not decreased under all the environments from low humidity to high humidity.

What is claimed is:

1. A fluorine containing diester of an alkyl- or alkenylsuccinic acid represented by the general formula:

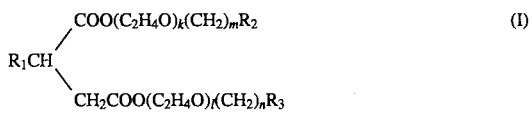
(I)

wherein $R_1$ represents an alkyl or alkenyl group, at least one of $R_2$ and $R_3$ is a fluoroalkyl or fluoroalkenyl group, the remaining of $R_2$ and $R_3$ are an alkyl or alkenyl group, k, l, m and n are each 0 or an integer of 1 to 20, respectively, and k+l is an integer of 2 to 20.

2. A fluorine containing diester of an alkyl- or alkenylsuccinic acid as claimed in claim 1, in which the $R_1$ group has 6 to 30 carbon atoms and the, $R_2$ and $R_3$ groups have 2 to 30 carbon atoms, respectively.

* * * * *